United States Patent
Kyllönen et al.

(10) Patent No.: US 10,920,149 B2
(45) Date of Patent: Feb. 16, 2021

(54) SURFACTANT COMPOSITION AND METHOD FOR TREATING BITUMEN FROTH

(71) Applicant: Kemira Oyj, Helsinki (FI)

(72) Inventors: Lasse Kyllönen, Espoo (FI); Sukhjit Aujla, The Woodlands, TX (US); Frances Fournier, Marietta, GA (US); Thomas Fenderson, Decatur, GA (US); Alistair King, Helsinki (FI); Evangelos Sklavounos, Helsinki (FI)

(73) Assignee: Kemira Oyj, Helsinki (FI)

( * ) Notice: Subject to any disclaimer, the term of this patent is extended or adjusted under 35 U.S.C. 154(b) by 53 days.

(21) Appl. No.: 15/735,181

(22) PCT Filed: Jun. 10, 2016

(86) PCT No.: PCT/FI2016/050414
§ 371 (c)(1),
(2) Date: Dec. 9, 2017

(87) PCT Pub. No.: WO2016/198747
PCT Pub. Date: Dec. 15, 2016

(65) Prior Publication Data
US 2018/0155628 A1    Jun. 7, 2018

Related U.S. Application Data

(60) Provisional application No. 62/174,553, filed on Jun. 12, 2015.

(30) Foreign Application Priority Data

Jun. 25, 2015  (FI) ..................... 20155501

(51) Int. Cl.
| *C10G 1/04* | (2006.01) |
| *C10C 3/00* | (2006.01) |
| *B03D 1/02* | (2006.01) |
| *C08L 95/00* | (2006.01) |
| *C09K 8/524* | (2006.01) |
| *C09K 8/584* | (2006.01) |
| *C07C 215/40* | (2006.01) |
| *C07C 279/04* | (2006.01) |
| *C11C 3/00* | (2006.01) |

(52) U.S. Cl.
CPC ............. *C10C 3/007* (2013.01); *B03D 1/026* (2013.01); *C08L 95/00* (2013.01); *C10G 1/04* (2013.01); *C10G 1/045* (2013.01); *C07C 215/40* (2013.01); *C07C 279/04* (2013.01); *C09K 8/524* (2013.01); *C09K 8/584* (2013.01); *C11C 3/00* (2013.01)

(58) Field of Classification Search
CPC .................................. C10G 1/04; C10G 1/045
See application file for complete search history.

(56) References Cited

U.S. PATENT DOCUMENTS

| 4,388,170 | A | * | 6/1983 | Schmid ..................... | C10G 1/00 |
| | | | | | 208/390 |
| 4,452,692 | A | * | 6/1984 | Kneissl ................... | C10G 47/02 |
| | | | | | 208/108 |
| 4,765,885 | A | * | 8/1988 | Sadeghi ................... | C10G 1/04 |
| | | | | | 208/390 |
| 6,019,888 | A | * | 2/2000 | Mishra ................... | C10G 1/045 |
| | | | | | 208/341 |
| 10,093,862 | B2 | * | 10/2018 | Kyllonen ............... | C10G 1/045 |
| 2005/0194292 | A1 | * | 9/2005 | Beetge ................... | C10G 1/047 |
| | | | | | 208/391 |
| 2006/0116296 | A1 | * | 6/2006 | Kippie ..................... | C09K 8/12 |
| | | | | | 507/244 |
| 2010/0256174 | A1 | | 10/2010 | Yamaguchi et al. | |
| 2012/0071371 | A1 | | 3/2012 | Zhang | |
| 2012/0255886 | A1 | * | 10/2012 | Flores Oropeza ..... | C10G 21/08 |
| | | | | | 208/188 |

FOREIGN PATENT DOCUMENTS

| CN | 103194193 A | 7/2013 |
| EP | 0640121 B1 | 7/1999 |
| EP | 2223703 A1 | 9/2010 |
| EP | 2266626 A1 | 12/2010 |
| WO | 2011161326 A2 | 12/2011 |
| WO | 2015066647 A2 | 5/2015 |

OTHER PUBLICATIONS

FI20155501 Search report dated Feb. 26, 2016, Finnish Patent Office.

* cited by examiner

*Primary Examiner* — Michelle Stein
(74) *Attorney, Agent, or Firm* — Robin L. Teskin; Baker, Donelson, Bearman, Caldwell & Berkowitz PC

(57) ABSTRACT

The invention relates to a surfactant composition comprising an ionic liquid prepared from an unsubsituted or substituted primary, secondary or tertiary amine, or from an unsubstituted or substituted pyridine, amidine or guanidine with at least one fatty acid and/or resin acid. The invention also relates to a method for treating bitumen froth from a separation process, where bitumen is separated from mineral solids. The method comprises addition of said surfactant composition to the diluent and/or to the froth before phase separation.

11 Claims, 3 Drawing Sheets

All figures:

- Bitumen recovery [%]
- Bitument water content [%]

SURFACTANT COMPOSITION AND METHOD FOR TREATING BITUMEN FROTH

PRIORITY

This application is a U.S. national application of PCT-application PCT/FI2016/050414 filed on Jun. 10, 2016 and claiming priority of U.S. provisional application 62/174,553 filed on Jun. 12, 2015 and Finnish national application FI 20155501 filed on Jun. 25, 2015, the contents of all of which are incorporated herein by reference.

The invention relates to a surfactant composition comprising an ionic liquid and a method for treating bitumen froth according to the preambles of the enclosed independent claims.

Oil sands, which are also known as tar sands, are mixtures of clay, sand, water, and heavy hydrocarbons, especially bitumen, and they provide a potential source of hydrocarbons for petrochemical industry. Many of the known processes for separating and recovering hydrocarbons from oil sands are, however, expensive. Some conventional bitumen extraction methods use a froth-flotation process to separate bitumen from mineral solids and water. In the process oil sand is mixed with heated water or steam, optionally also with caustic solution. Mixing results in formation of two fractions, where the first fraction is bitumen froth, which comprises bitumen, water and small amount of mineral solids. The second fraction comprises mainly water and mineral solids. The two fractions are separated from each other and the bitumen froth fraction is processed further for recovery of the bitumen.

In the further processing the bitumen froth is diluted with a suitable hydrocarbon solvent in order to reduce the viscosity and density of the bitumen oil phase, which accelerates the separation of the solid impurities, for example by gravity. The separated bitumen from the froth-flotation process should contain so small amounts of water and mineral solids as possible, preferably <2 weight-% and <0.5 weight-%, respectively. If the amount of water and/or minerals solids is too high, the bitumen is not directly suitable for pipelining or further refining. Sometimes the process operators are forced to slow down the froth treatment in order to achieve acceptable low levels of water and mineral solids in the separated bitumen. One or more additional process steps may also be required for upgrading the separated bitumen to an acceptable quality level. All this naturally complicates the production and increases the production costs. Similar problems may also be related to recovery of oil from oil shale.

Surfactants may be used in froth-flotation process to separate mineral solids and water from bitumen froth.

There exists a need to improve methods for treating bitumen froth for separation of mineral solids and water from bitumen.

An object of this invention is to minimise or even totally eliminate the disadvantages existing in the prior art.

Another object of the present invention is to provide a simple method for treating bitumen froth from a separation process.

A further object of the present invention is to improve separation of water and especially mineral solids from bitumen in a surfactant assisted froth treatment.

Another further object of the present invention is to provide a surfactant composition, which is easily biodegradable, non-toxic and provides good separation results in treatment of bitumen froth.

The invention is defined in the characterising parts of the enclosed independent claims. Some preferable embodiments of the invention are defined in the dependent claims. All described features apply both for the composition, its use as well as the method of the invention, whenever applicable, even if it not necessarily always stated so.

Typical surfactant composition according to the present invention comprises at least one ionic liquid prepared from an unsubsituted or substituted primary, secondary or tertiary amine, or from an unsubstituted or substituted pyridine, amidine or guanidine with at least one fatty acid and/or resin acid.

Typical use of a surfactant composition according to the present invention is for separation of bitumen from an aqueous phase and mineral solids phase.

Typical method according to the present invention for treating bitumen froth from a separation process, where bitumen is separated from mineral solids, comprises
 obtaining bitumen froth that comprises bitumen, water and mineral solids,
 adding organic diluent, such as naphthenic or paraphenic solvent, to the froth,
 providing a phase separation between an organic phase, aqueous phase and solid phase, and
 adding a surfactant composition according to the present invention to the diluent and/or to the froth before the phase separation in amount of less than 1500 ppm, preferably less than 1000 ppm.

Now it has been found that a surfactant composition comprising ionic liquid can provide an efficient phase separation between water, bitumen and mineral particles in bitumen froth. The origin of the phenomenon is not yet fully understood, and it is surprising that even an addition of relatively small amount of surfactant composition, which comprises ionic liquid, to the bitumen froth may enable a good phase separation, especially the separation of particles of mineral solids. Furthermore, use of surfactant composition comprising ionic liquid facilitates a significant reduction in water content of the produced bitumen and/or significant improvement in bitumen recovery.

In the present context the term "bitumen" is understood as a highly viscous mixture of crude oil, comprising hydrocarbons heavier than pentanes, and which mixture has a viscosity above 10 000 cP, and is non-mobile at reservoir conditions. Bitumen may have an API gravity<12°, preferably <10°, more preferably <8°. The API gravity of bitumen may be in the range of 12°-6°. Bitumen may comprise >15 weight-%, preferably >25 weight-%, of asphaltenes. The total amount of asphaltenes and resins in bitumen may be >40 weight-%, preferably >45 weight-%. The bitumen froth may comprise 30-75 weight-% of bitumen, 15-35 weight-% of water and 5-20 weigh-% of mineral solids before the phase separation step.

Surfactants comprising ionic liquid are relatively simple to manufacture, as the synthesis of ionic liquid is not complicated. This means that the surfactant composition may be manufactured on-site, if needed. The raw materials for the ionic liquid component may be delivered as solid products.

Ionic liquids are non-flammable and thermally stable. Therefore surfactants which comprise ionic liquids are safe to handle and transport and minimize the occupational hazards during their use. The surfactant composition according to the present invention can be used even in harsh environments at high temperatures and alkaline conditions.

In the present context the term "ionic liquid" is understood to denote an ionic salt-like material, which is liquid at temperature of <100° C., preferably temperature of <50° C., at atmospheric pressure. Ionic liquids include two components, namely a cationic component and an anionic component. The ionic liquids suitable for use in the present invention are soluble in water and insoluble in non-polar organic solvents. The ionic liquids are preferably biodegradable. In this context compounds and compositions are referred biodegradable if they reach a biodegradation level higher than 60%, evaluation being based on the so-called BODS (Biochemical oxygen demand after 5 days) or "Closed Bottle Test" (OECD 301 D).

Ionic liquids suitable for use in the present invention may be reversible, which means that they can be easily recycled and reused, which may improve the process economy. Reversible ionic liquid means that the molecular components forming the ionic liquid can be transformed into ionic liquid and vice versa, either by application of heat, vacuum or by bubbling suitable gas, such as $N_2$ or suitable acid gas, such as $CO_2$, in the mixture of components. It may also be possible to dissociate the ionic liquid by using acid-base chemistry. Preferably the reversible ionic liquid may be a combination of dissociated acid and base, which can be converted back to distillable acid and base forms by application of heat. Ionic liquids where the positive charge cannot be removed, such as 1,3-dialkylimidazoliums, tetraalkylphosphoniums, trialkylsulphoniums and tetraalkylammoniums are preferably excluded from the ionic liquids which are used in the present invention.

The surfactant composition comprises at least one ionic liquid prepared from an unsubsituted or substituted primary, secondary or tertiary amine, such as tributylamine; or from an unsubsituted or substituted pyridine, amidine or guanidine together with a fatty acid or rosin acid. According to one preferable embodiment of the present invention the ionic liquid is prepared from substituted tertiary amine which is choline or from substituted guanidine, which is tetramethylguanidine (TMG). According to one embodiment the substituted guanidine is 1,1,2,3,3,-pentamethylguanidine (PMG) or 2-butyl-1,1,3,3-tetramethyl guanidine (BTMG). It was observed that these ionic liquids provided unexpectedly effective separation of the organic phase, which mainly comprises bitumen, from the mineral solids phase.

The surfactant composition may also comprise a plurality of, i.e. two or more, different ionic liquids.

The surfactant composition comprises also at least one fatty and/or resin acid. According to one embodiment of the invention the surfactant composition comprises a mixture of fatty acids and/or resin acids. Suitable fatty acids may be saturated or unsaturated, and they can be branched or linear. Examples of suitable fatty acids are stearic acid, hexanoic acid and isostearic acid. According to one preferable embodiment of the invention the fatty acid is selected from stearic acid or isostearic acid. By proper selection of fatty and/or resin acids the properties of the surfactant composition may be tailored to provide optimal phase separation between the organic bitumen phase, the aqueous phase and the mineral solids phase.

Fatty acid, which may be used in the surfactant composition, may originate from Kraft pulp process or from biodiesel production. Alternatively fatty acid may originate from natural and/or agricultural sources, and it can originate from oil crops, such as rapeseed oil, linseed oil, sunflower oil, soya oil or any mixture thereof. According to one preferable embodiment the fatty acid may be tall oil fatty acid (TOFA), preferably originating from Kraft pulp process or from biodiesel production.

According to one preferable embodiment of the invention the resin acid is rosin acid.

According to one embodiment of the invention the molar ratio between the cationic component, i.e. amine, pyridine, amidine or guanidine, and the anionic component, i.e. fatty acid/resin acid, may be 1:1. In some embodiments the molar amount of the cationic component may be higher than the molar amount of anionic component, i.e. fatty acid/resin acid.

According to one embodiment of the invention an organic diluent is added to the bitumen froth that contains bitumen, mineral solids and water. The organic diluent may be naphthenic or paraphenic solvent, such as toluene or pentane. The surfactant composition may be added to the organic diluent before it is added to the bitumen froth, or the surfactant composition may be added to the froth after the addition of the organic diluent. The surfactant composition may be added in amount of less than 1500 ppm, preferably less than 1000 ppm. According to one embodiment of the invention the surfactant composition is added in amount of 5-1500 ppm, preferably 10-1000 ppm, more preferably 10-500 ppm or 10-300 ppm, even more preferably 10-200 ppm. The amount of surfactant composition is calculated on the basis of the total weight of both the froth and the organic diluent.

The phase separation between the organic phase, aqueous phase and solid phase may be performed by using centrifugation, which may be followed by gravity settling, or by using gravity settling alone.

According to one embodiment of the present invention the bitumen froth originates from a process that use oil sand, oil shale, oil contaminated sand or oil contaminated earth, tailing pond material and/or sand containing crude oil as raw material. The bitumen froth may comprise 30-75 weight-%, preferably 40-70 weight-%, of bitumen; and 15-35 weight-% of water; as well as 5-20 weight-%, preferably 5-15 weight-%, of mineral solids before the phase separation step.

According to one embodiment the present invention is especially suitable for treating bitumen froth from oil sand processing. Oil sand is a mixture, which comprises hydrocarbons, such as semi-solid crude bitumen, water and mineral solids, such as silica sands and clay minerals. Oil sand may comprise 80-90 weight-%, preferably 82-90 weight-%, of mineral solids, such as mineral particles, and 1-18 weight-%, preferably 1-10 weight-% of hydrocarbons.

The organic phase after the phase separation step may comprise 83-95 weight-%, preferably 85-95 weight-%, of bitumen; and 0.1-0.5 weight-%, preferably 0.1-0.3 weight-%, of water; as well as 0.0-0.5 weight-%, preferably 0.01-0.2 weight-%, of mineral solids. The obtained organic phase from the present process may be used for manufacture of synthetic crude oil. The obtained bitumen may be processed further e.g. for removal of excess carbon and for addition of hydrogen.

EXPERIMENTAL

Preparation of Froth Samples

Froth sample was obtained from an industrial process. During the transport to the laboratory the sample was phase-separated. In the laboratory the froth sample was homogenized by using a 5 dm$^3$ glass jacketed reactor equipped with stirrer over 3 hours under heating at 90° C. The froth sample comprised 10.6 weight-% of solid matter, 65.0 weight-% of bitumen and 24.4 weight-% of water.

Tested Ionic Liquids

Following ionic liquids were tested as surfactants:
N,N,N,N-tetramethylguanidinium stearate [TMG][Ster]
N,N,N,N-tetramethylguanidinium isostearate [TMG][iSter]
N,N,N,N-tetramethylguanidinium rosin [TMG][Ros]
Guanidine isostearate [Gd][iSter]
Choline isostearate [Ch][iSter]

Mixing of Froth with Surfactant/Toluene Solution and Centrifugation

Homogenized froth was removed from the glass jacketed reactor through the bottom valve into a glass beaker. 31 g of homogenized froth was transferred into each 50 ml Falcon centrifuge sample tubes while still hot. Approximately 8 g of surfactant/toluene solution was quickly added to maintain a surfactant/toluene:froth ratio of 1:3.9 or surfactant/toluene:bitumen ratio of 1:2.5. A blank sample comprising only toluene and froth and a reference sample comprising froth and a commercial surfactant comprising sodium dodecyl sulfate were also prepared at similar conditions.

Phase Separation and Bitumen Recovery

The Falcon centrifuge sample tubes were shaken vigorously by hand for a few minutes and then placed in a centrifuge to perform separation of the toluene-bitumen phase from the other froth constituents. Centrifugation was performed at 40° C. at 3000 rpm for 20 minutes. Solid material appeared in the bottom of the tube as a separate phase. The Falcon centrifuge sample tubes were allowed to rest for approximately 30 min. No visible phase separation of toluene-bitumen phase was observed. The liquid phase was removed to a second Falcon centrifuge sample tube where the phase separation is observed from bottom to top as follows: 0.1-2 ml of solid residue, 0.5-6.5 ml of clear liquid phase, 22-27 ml of toluene-bitumen phase.

Primary bitumen recovery is defined by measuring the volume of the bitumen-toluene phase in the second Falcon centrifuge sample tube by using the volumetric scale of the tube and using the known density of the bitumen sample in the calculations. Highly viscous bitumen remaining on top of the solid material layer in the first Falcon centrifuge sample tube used in the centrifugation was collected to form the secondary recovery of bitumen. Total bitumen recovery comprises both the primary bitumen recovery and the secondary bitumen recovery.

Samples for determining the water content by Karl Fischer analysis and solid matter content in toluene-bitumen phase were taken from the middle of the toluene-bitumen layer from the primary bitumen recovery.

Results

Figure 1:
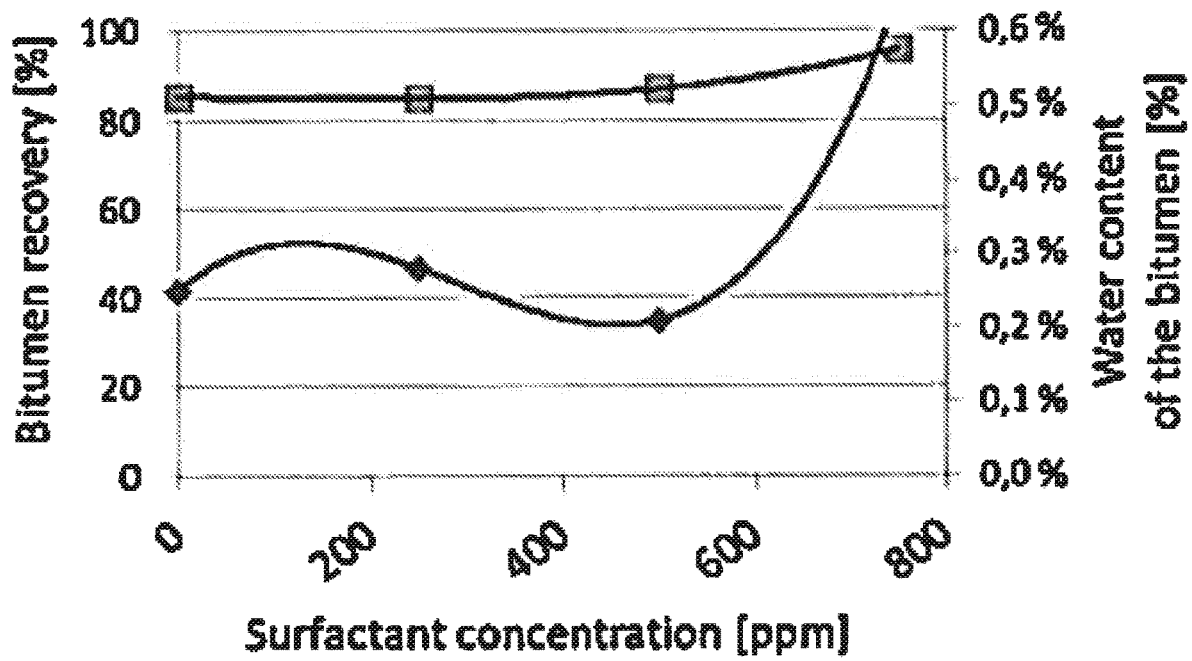
FIG. 1 presents the bitumen recovery and water content results for [TMG][Ster] when used as surfactant.

The bitumen recovery and water content results for [TMG][Ster] when used as surfactant are presented in FIG. 1. The results indicate that it is possible to provide 10.5% higher bitumen recovery with [TMG][Ster], used as 750 ppm concentration. At the same time, however, the water content in bitumen increases 2.56 fold. The optimum dosage was estimated to be somewhat lower, namely 500 ppm. This results a bitumen recovery which is 1.7% higher and a water content, which is 16% lower than the corresponding values for the reference sample.

Figure 2:
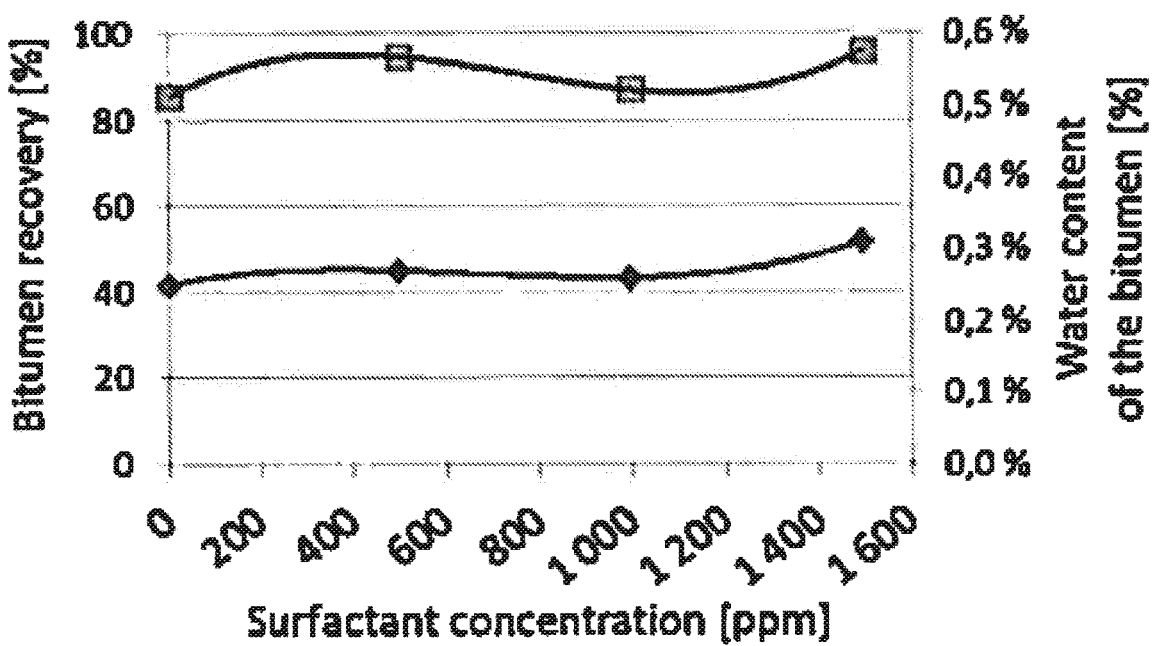
FIG. 2 presents the bitumen recovery and water content results for [TMG][iSter] when used as surfactant.

The bitumen recovery and water content results for [TMG][iSter] when used as surfactant are presented in FIG. 2. The results indicate a higher bitumen recovery and relatively stable water content throughout the concentration series. The optimum dosage was estimated to be 500 ppm also for [TMG][iSter]. This concentration results a bitumen recovery which is 9.4% higher and a water content, which is only 8% higher than the corresponding values for the reference sample.

Figure 3:
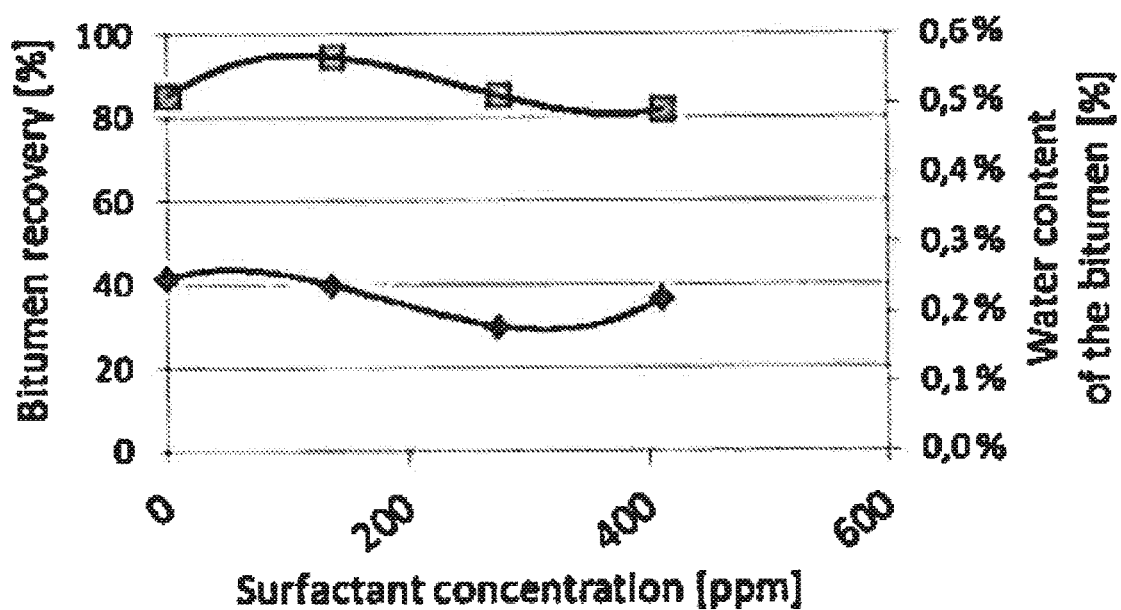
FIG. 3 presents the bitumen recovery and water content results for [TMG][Ros] when used as surfactant.

The bitumen recovery and water content results for [TMG][Ros] when used as surfactant are presented in FIG. 3. The optimum dosages were estimated to be drastically lower, either 137 ppm, which resulted 9.5% higher bitumen recovery with identical bitumen water content, or 274 ppm, which resulted identical bitumen recovery but 28% lower water content. This provides further degrees of freedom, depending whether the bitumen recovery or water content is of primary interest.

Figure 4:
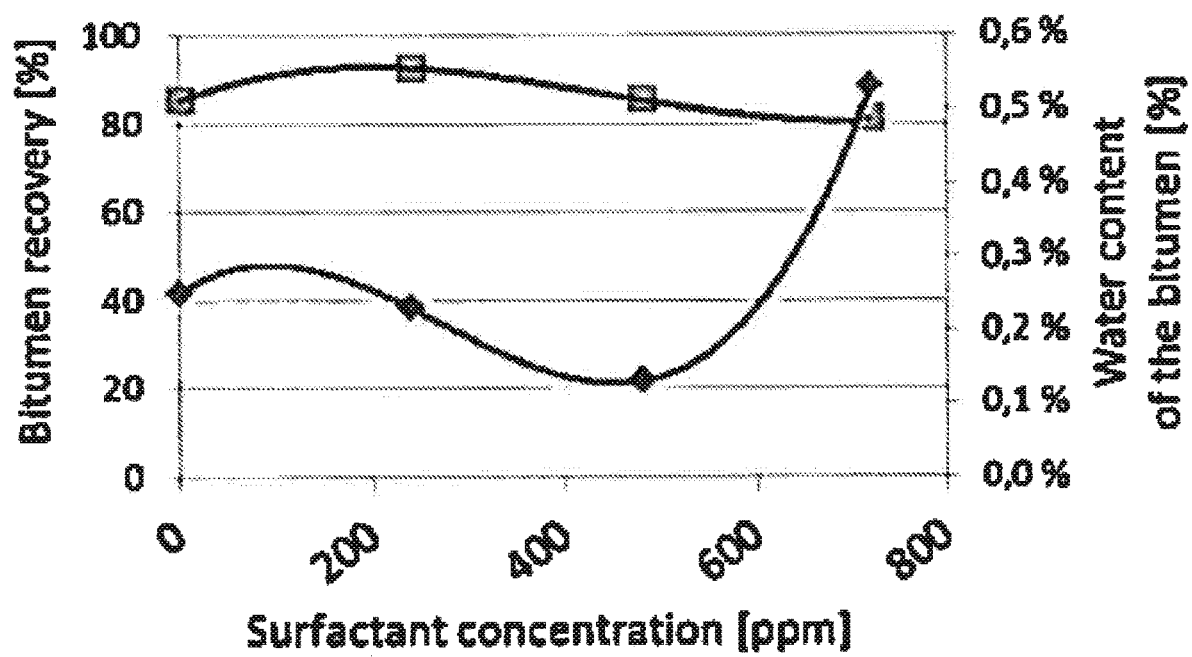
FIG. 4 presents the bitumen recovery and water content results for [Gd][iSter] when used as surfactant.

The bitumen recovery and water content results for [Gd][iSter] when used as surfactant are presented in FIG. 4. The optimum dosages were estimated to be either 240 ppm, which resulted a bitumen recovery which is 7.5% higher with similar water content, or 480 ppm, which resulted identical bitumen recovery but 48% lower water content than the corresponding value for the reference sample.

Figure 5:
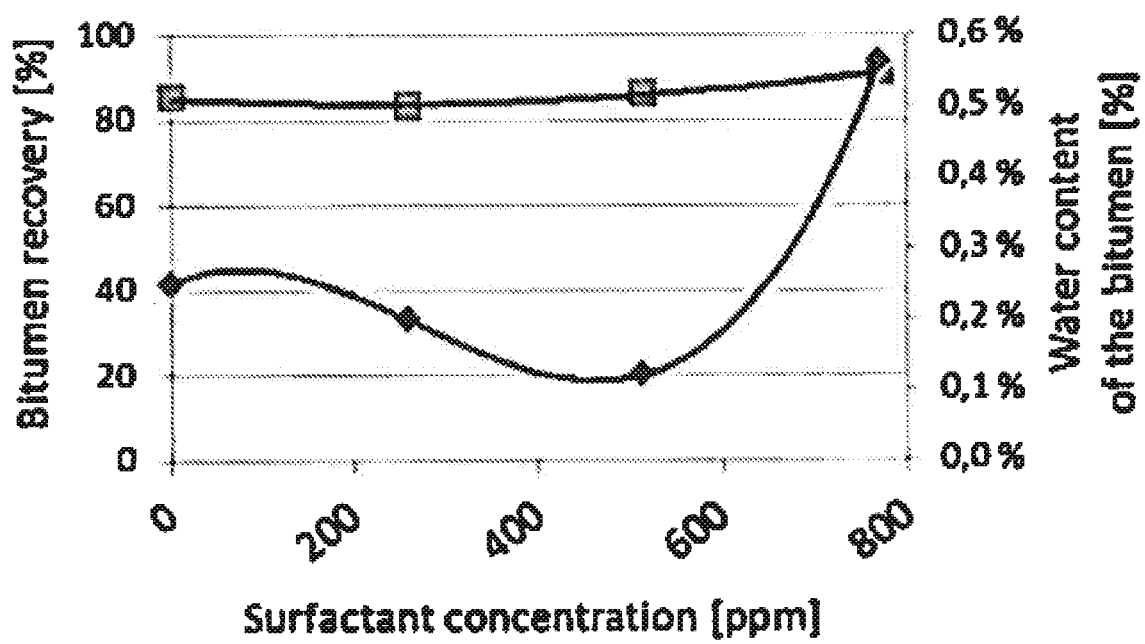
FIG. 5 presents the bitumen recovery and water content results for [Ch][iSter] when used as surfactant.

The bitumen recovery and water content results for [Ch][iSter] when used as surfactant are presented in FIG. 5. The optimum dosage was estimated to be 514 ppm, which resulted 52% lower water content than the corresponding value for the reference sample.

CONCLUSIONS

All ionic liquids comprising tetramethylguanidinium are able to provide higher bitumen recovery than the corresponding reference sample, but may cause increase in bitumen water content. One of the promising alternatives seem to be [TMG][Ros] which provides a positive response at significantly lower dosages. Furthermore [TMG][Ros] can provide significant improvement either in bitumen recovery, with increase by 9.5% units, or in water content with reduction of 28% units, depending on which parameter is more critical in the process. Results obtained with [Gd][iSter] and [Ch][iSter] are particularly interesting for operators who are suffering from high bitumen water content. These ionic liquids were able to provide a reduction of approximately 50% in water content, compared to corresponding value of the reference sample.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method for treating bitumen froth from a separation process, where bitumen is separated from mineral solids, the method comprising:
    (i) obtaining a bitumen froth that comprises bitumen, water and mineral solids;
    (ii) adding organic diluent to the bitumen froth;

(iii) causing a phase separation of the water, bitumen and mineral particles comprised in the diluted bitumen froth by the addition of less than 1500 ppm of a surfactant composition:
  (a) which surfactant composition comprises at least one ionic liquid that includes choline and at least one fatty acid and/or resin acid; and/or
  (b) which surfactant composition comprises at least one ionic liquid that includes an unsubstituted or substituted pyridine, amidine, or guanidine and at least one fatty acid and/or resin acid.

2. The method according to claim 1, wherein the surfactant composition is added in amount of 5-1500 ppm, 10-1000 ppm, or 10-500 ppm.

3. The method according to claim 1, wherein the separation process, where bitumen is separated from mineral solids, uses oil sand, oil shale, oil contaminated sand or oil contaminated earth, tailing pond material and/or sand containing crude oil as raw material.

4. The method according to claim 1, wherein the obtained bitumen froth comprises 30-75 weight-% of bitumen, 15-35 weight-% of water and 5-20 weight-% of mineral solids before the phase separation step.

5. The method according to claim 1, wherein the organic phase comprises 83-95 weight-% of bitumen, 0.1-0.5 weight-% of water and 0.0-0.5 weight-% of mineral solids after the phase separation step.

6. The method according to claim 1, wherein causing the phase separation further comprises centrifugation and/or gravity settling.

7. The method according to claim 1, wherein the surfactant composition comprises a mixture of fatty acids and/or resin acids.

8. The method according to claim 1, wherein the fatty acid is selected from stearic acid or isostearic acid.

9. The method according to claim 1, wherein the fatty acid originates from Kraft pulp process or from biodiesel production.

10. The method according to claim 1, wherein the substituted guanidine is tetramethylguanidine (TMG).

11. The method according to claim 1, wherein the surfactant composition comprises two or more different ionic liquids.

* * * * *